United States Patent [19]

Ruland et al.

[11] Patent Number: 4,603,224
[45] Date of Patent: Jul. 29, 1986

[54] PREPARATION OF KETENE O,O-ACETALS

[75] Inventors: Alfred Ruland, Hirschberg; Wolfgang Reuther, Heidelberg, both of Fed. Rep. of Germany

[73] Assignee: BASF Aktiengesellschaft, Fed. Rep. of Germany

[21] Appl. No.: 743,681

[22] Filed: Jun. 11, 1985

[30] Foreign Application Priority Data

Jun. 15, 1984 [DE] Fed. Rep. of Germany ....... 3422217

[51] Int. Cl.$^4$ ...................... C07C 41/08; C07C 43/166
[52] U.S. Cl. .................................................... 568/592
[58] Field of Search ......................................... 568/592

[56] References Cited

PUBLICATIONS

Borrmann, Houben–Weyl–Muller, Methoden der organischen Chemie, vol. 7/4, pp. 340 et seq.

*Primary Examiner*—Bernard Helfin
*Attorney, Agent, or Firm*—Keil & Weinkauf

[57] ABSTRACT

Ketene O,O-acetals which can be converted in a simple manner to fungicidal ketene O,N-acetals are prepared by an addition reaction of a phenol with a phenoxyalkyne.

1 Claim, No Drawings

PREPARATION OF KETENE O,O-ACETALS

The present invention relates to a process for the preparation of ketene O,O-acetals by reacting a phenoxyalkyne with a phenol. They can be very readily further processed to fungicidal ketene O,N-acetals.

Several processes have been disclosed for the preparation of ketene O,O-acetals (D. Borrmann in Houben-Weyl-Müller, Methoden der organischen Chemie, volume 7/4, page 340 et seq., Thieme Verlag, Stuttgart 1968):

1. Elimination of hydrogen halide from alpha-haloacetals with alkali metal alcoholates, in particular potassium tert.-butylate. However, this process has some disadvantages. On the one hand, this process gives only ketene O,O-acetals which are unsubstituted or monosubstituted by chlorine, bromine or phenyl in poor to moderate yields; for example, the yield falls to as low as 22% in the case of isopropylketene diethylacetal. On the other hand, the alcohol components in question are virtually exclusively simple aliphatic alcohols, such as methanol and ethanol. Furthermore, the alpha-haloacetals required for the synthesis of more highly substituted ketene O,O-acetals using phenols as alcohol components are unknown to date and, because of various side reactions, are probably unobtainable.

2. In another conventional process, alcohols are eliminated from triesters of orthocarboxylic acids. The preparation of the required orthocarboxylates using phenols as alcohol components makes this process too impossible to use in practice. The same restriction also applies to the synthesis of ketene O,O-acetals by elimination of an alkyl hypobromite from triesters of alpha-bromocarboxylic acids.

3. The conversion of 1,1-dihaloethylenes to ketene O,O-acetals is also known. However, these reactions can be carried out successfully only in the case of beta-activated ethylenes or in the special case of 1,1-dichloroethylene, by reaction with beta- or gamma-alkoxy or dialkylamino alcoholates.

4. In another conventional process, diphenoxyketene O,O-acetals are prepared from the corresponding alpha-hydroxyacetals by tosylation of the hydroxyl group and subsequent elimination. Although this process gives good yields, the tosylation step, which can only be carried out using relatively expensive starting materials, such as sodium hydride or the like, makes it uneconomical for use in industrial production.

It is an object of the present invention to improve the preparation of the ketene O,O-acetals which are of interest as intermediates, for example in the synthesis of fungicides based on ketene O,N-acetals.

We have found that this object is achieved, and that the stated disadvantages of the above processes can be overcome, if a phenoxyalkyne of the formula II

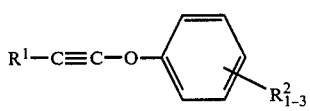

where $R^1$ and $R^2$ have the meanings stated for formula I, is reacted with a phenol of the formula III

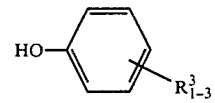

where $R^3$ likewise has the meaning stated for formula I, in the presence of a Friedel-Crafts catalyst.

Alkyl of 1 to 6 carbon atoms is methyl, ethyl, n-propyl, isopropyl, n-, iso- or tert.-butyl, pentyl or hexyl, and halogen in this case is fluorine, bromine or, preferably chlorine.

The reaction of the phenoxyalkynes of the formula II with phenols of the formula III according to the equation

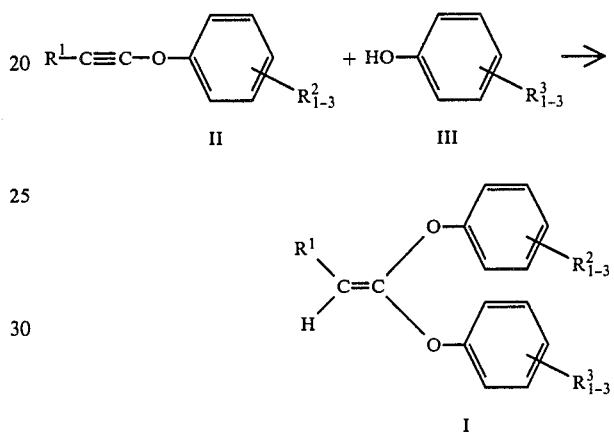

takes place in a polar, high-boiling, aprotic solvent, such as dimethylformamide, dimethyl sulfoxide, N-methylpyrrolidone or sulfolane, preferably in the melt, at from 100° to 200° C., preferably from 150° to 170° C., in the presence of a Friedel-Crafts catalyst, such as AlCl$_3$, BF$_3$, SnCl$_4$, TiCl$_4$, CdCl$_2$ or, preferably, ZnCl$_2$. $R^2$ and $R^3$ are each preferably chlorine, particularly where each phenyl nucleus is polysubstituted (disubstituted or trisubstituted) by them. $R^2$ and $R^3$ can each be in the 2-, 3- or, preferably, 4-position. Where the phenyl nucleus is disubstituted by these radicals, the positions 2,4 and 3,5 are preferred, while in the case of trisubstitution 2,4,5 is preferred. However, other combinations of positions are also possible.

The product is only pure when the phenyl nuclei in the phenoxyalkyne II and in the phenol III are substituted in the same manner. Otherwise, mixtures are formed, the preparation of which is likewise claimed. In the simplest case, the components of the mixtures consist only of the cis and trans isomers. However, depending on the reaction conditions, it is also possible for exchange of the phenyl nuclei to occur to a greater or lesser extent, in which case more complicated mixtures (consisting of 4 components) are formed.

Although reactions of alkoxyalkynes with alcohols or phenols are known in principle, for example from V. Jëger and H. G. Viehe, Methoden der org. Chemie, Houben-Weyl-Müller, Thieme Verlag, Stuttgart 1977, volume 5/2a, page 740, they lead only to mixed aliphatic aromatic ketene O,O-acetals, and further reaction to give the corresponding ortho esters occurs readily. Moreover, the only reactions of this type which have been described are those involving unsubstituted alkoxyalkynes. The virtually quantitative reaction of substituted phenoxyalkynes with phenols to give the corresponding diphenoxyketene O,O-acetals is therefore all the more surprising.

The great advantage of this procedure is that the required phenoxyalkynes of the formula II are readily obtainable (cf. for example European Patent Application 84101877.3) and their reaction with phenols of the formula III according to the present invention takes place virtually quantitatively to give the desired compounds of the formula I, so that, as a rule, no additional purification is required for further conversion to the fungicidal ketene O,N-acetals. This lastmentioned reaction is carried out in the melt at about 180°–200° C., in accordance with European Patent Application 83110592.9-2101.

In European Patent Application 84101877.3, the preparation of the phenoxyalkynes of the formula II is described as follows:

In the process for the preparation of an alkyl-substituted phenoxyacetylene of the formula

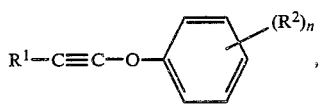

where $R^1$ is alkyl of 1 to 8 carbon atoms, $R^2$ is halogen, alkyl of 1 to 4 carbon atoms, alkoxy of 1 to 4 carbon atoms, cyano, nitro, trifluoromethyl, phenyl or phenoxy, it being possible for the phenyl or phenoxy radical itself to be substituted by halogen or alkyl of 1 to 4 carbon atoms, and n is 0 or an integer from 1 to 5, wherein (a) a 1,1-dihalo-olefin of the formula II

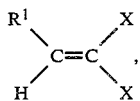

where $R^1$ has the above meaning and X is halogen, is reacted with an alkali metal, alkaline earth metal or aluminum phenolate of the formula

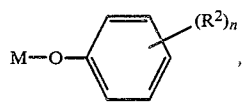

where $R^2$ and n have the meanings and M is one equivalent of an alkali metal, alkaline earth metal or aluminum atom, in the presence of a copper salt or a copper compound and a polar solvent at a temperature of from 50° to 250° C. to give an α-halo-enol ether of the formula III

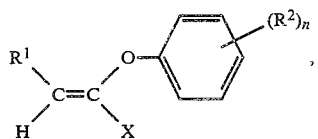

where $R^1$, $R^2$, X and n have the above meanings, and (b) the compound of the formula III is reacted in the presence of a base and a solvent at a temperature of from −40° to +100° C., with the elimination of hydrogen halide, to give the alkyl-substituted phenoxyacetylene of the formula

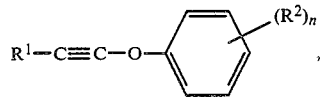

where $R^1$, $R^2$ and n have the above meanings.

In European Patent Application 83110592.9-2101, the conversion of the compounds of the formula I to the fungicidal ketene O,N-acetals is described as follows:

Ketene O,O-acetals where OR is the phenol radical are reacted with heterocyclic compounds, e.g. triazole or imidazole, to give ketene O,N-acetals in virtually quantitative yield and with high stereoselectivity, without significant formation of ketene N,N-acetals.

To carry out the example, stoichiometric amounts of the ketene O,O-acetal and the amine are initially taken, and the mixture is heated at the reaction temperature, while stirring thoroughly (two-phase systems are formed in some cases). The reaction temperature is from 100° to 250° C., preferably from 180° to 200° C. The increasing homogenization of the mixture and elimination of phenol permit the beginning of the reaction, and its course, to be monitored. Advantageously, samples are taken from the reaction mixture at particular intervals, and the course of the reaction is monitored by means of gas chromatography or HPLC.

The reaction is terminated as soon as starting material is no longer present. The mixture is usually worked up by extracting the eliminated phenol from the organic solution of the end product, using an aqueous basic extracting agent, e.g. sodium hydroxide solution or potassium hydroxide solution, preferably in a concentration of from 5 to 30% by weight in water. Suitable organic solvents are aliphatic hydrocarbons, ethers or esters and aromatic hydrocarbons, e.g. toluene or o, m or p-xylene. However, it is also possible to extract the end product as a quaternary ammonium salt from the organic phase, preferably using an aqueous solution of a strong inorganic acid, e.g. hydrochloric acid, hydrobromic acid, sulfuric acid, nitric acid or perchloric acid. After neutralization of the acid, the free ketene O,N-acetal can be isolated from the aqueous phase.

EXAMPLE 1

1,1-Bis-(2,4-dichlorophenoxy)-3,3-dimethylbut-1-ene 24.3 g (0.1 mole) of 1-(2,4-dichlorophenoxy)-3,3-dimethylbut-1-yne were initially taken together with 16.3 g (0.1 mole) of 2,4-dichlorophenol and 1.4 g (0.01 mole) of zinc chloride, and the stirred mixture was heated at 160° C. After 30 minutes, the phenol had reacted quantitatively with the phenoxyalkyne to give 1,1-bis-(2,4-dichlorophenoxy)-3,3-dimethylbut-1-ene.

$^1$H-NMR data (trimethylsilane, in $CDCl_3$): δ=1.2 (s, 9H); 4.95 (s, 1H); 7.73 (m, 6H)

EXAMPLE 2

1,1-Bis-(4-chlorophenoxy)-3,3-dimethylbut-1-ene 31.3 g (0.15 mole) of 1-(4-chlorophenoxy)-3,3-dimethylbut-1-yne were initially taken together with 19.3 g (0.15 mole) of 4-chlorophenol and 1.4 g (0.01 mole) of tin(IV) chloride, and the stirred mixture was heated at 160° C. until the phenoxyalkyne was no longer detectable by high pressure liquid chromatography. This was the case after 20 to 60 minutes.

$^1$H-NMR: =1.2 (s, 9H); 4.8 (s, 1H); 6.8–7.4 (m, 8H)

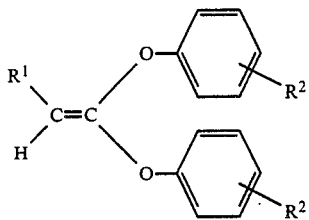

The compounds of Examples 3 to 7 were prepared in a similar manner:

| Example | $R^1$ | $R^2, R^3$ | $^1$H-NMR data δ values in CDCl$_3$ |
|---|---|---|---|
| 3 | + | 2-Cl | δ = 1.2 (s,9H); 4.8 (s,1H); 6.8–7.4 (m,8H) |
| 4 | + | 4-Br | δ = 1.15 (s,9H); 4.8 (s,1H); 6.8–7.1 (m,6H) |
| 5 | + | 3,5-Cl$_2$ | δ = 1.15 (s,9H); 4.95 (s,1H); 6.8–7.1 (m,6H) |
| 6 | + | 2,4,5-Cl$_3$ | δ = 1.2 (s,9H); 4.95 (s,1H); 7.25–7.5 (m,4H) |
| 7 | –⌬ | $R^2$ = 2,4-Cl$_2$ $R^3$ = 4-Cl | δ = 5.8 (s,1H); 7.1–7.8 (m,12H); 5.9 (s,1H); 7.1–7.8 (m,12H); E/Z isomer mixture |

We claim:

1. A process for the preparation of a ketene O,O-acetal of the formula I

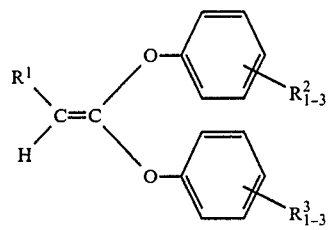

where $R^1$ is alkyl of 1 to 6 carbon atoms or phenyl which is unsubstituted or substituted by halogen or phenyl, and $R^2$ and $R^3$ independently of one another are each chlorine, bromine or phenyl, wherein an alkyne of the formula II

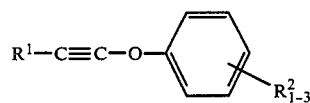

where $R^1$ and $R^2$ have the meanings stated for formula I, is reacted with a phenol of the formula III

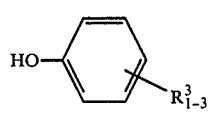

where $R^3$ likewise has the meanings stated for formula I, in the presence of a Friedel-Crafts catalyst.

* * * * *